(12) United States Patent
Campbell et al.

(10) Patent No.: US 6,646,218 B1
(45) Date of Patent: Nov. 11, 2003

(54) MULTI-BAND SPECTRAL SORTING SYSTEM FOR LIGHT-WEIGHT ARTICLES

(75) Inventors: Duncan Campbell, Central Point, OR (US); Todd Hoffman, Medford, OR (US); Cliff Leidecker, Rogue River, OR (US); H. Parks Squyres, Medford, OR (US)

(73) Assignee: Key Technology, Inc., Walla Walla, WA (US)

( * ) Notice: Subject to any disclaimer, the term of this patent is extended or adjusted under 35 U.S.C. 154(b) by 0 days.

(21) Appl. No.: 09/937,804

(22) PCT Filed: Mar. 29, 2000

(86) PCT No.: PCT/US00/08384

§ 371 (c)(1),
(2), (4) Date: Dec. 18, 2001

(87) PCT Pub. No.: WO00/58035

PCT Pub. Date: Oct. 5, 2000

Related U.S. Application Data
(60) Provisional application No. 60/126,772, filed on Mar. 29, 1999.

(51) Int. Cl.[7] .............................. B07C 5/342; G01J 3/51; G10N 21/35
(52) U.S. Cl. ....................... 209/582; 209/577; 209/587; 209/906; 356/51; 356/419; 356/425
(58) Field of Search ................................. 209/576, 577, 209/580, 581, 582, 587, 585, 906; 356/419, 421, 425, 51

(56) References Cited

U.S. PATENT DOCUMENTS

| | | | | |
|---|---|---|---|---|
| 3,854,586 A | * | 12/1974 | Perkins, III .................. | 209/565 |
| 4,057,352 A | * | 11/1977 | Babb ........................... | 356/407 |
| 4,186,836 A | * | 2/1980 | Wassmer et al. ............. | 209/565 |
| 4,203,522 A | * | 5/1980 | Fraenkel et al. ............. | 209/558 |
| 4,225,242 A | * | 9/1980 | Lane ............................ | 356/407 |
| 4,308,959 A | | 1/1982 | Hoover et al. ............... | 209/563 |
| 4,558,786 A | * | 12/1985 | Lane ............................ | 209/558 |
| 4,609,108 A | | 9/1986 | Hristozov et al. ........... | 209/581 |
| 4,735,323 A | | 4/1988 | Okada et al. ................. | 209/582 |
| 5,158,181 A | * | 10/1992 | Bailey .......................... | 209/558 |
| 5,239,176 A | | 8/1993 | Stevenson ............... | 250/227.25 |
| 5,241,171 A | * | 8/1993 | Fraenkel ................ | 250/223 R |
| 5,286,980 A | | 2/1994 | Richert ........................ | 250/560 |
| 5,314,072 A | * | 5/1994 | Frankel et al. .............. | 209/44.1 |
| 5,462,176 A | * | 10/1995 | Hereford et al. ............ | 209/577 |
| 5,464,981 A | | 11/1995 | Squyres et al. ........... | 250/341.8 |
| 5,479,065 A | * | 12/1995 | Sugimoto et al. ........... | 313/113 |
| 5,487,472 A | * | 1/1996 | Satake et al. ................ | 209/581 |
| 5,779,058 A | * | 7/1998 | Satake et al. ................ | 209/581 |
| 5,791,497 A | * | 8/1998 | Campbell et al. ........... | 209/577 |
| 5,794,788 A | * | 8/1998 | Massen ........................ | 209/524 |
| 5,841,546 A | | 11/1998 | Carangelo et al. .......... | 356/445 |
| 5,864,210 A | | 1/1999 | Hochi et al. ................. | 313/641 |
| 5,873,470 A | * | 2/1999 | Davis et al. ................. | 209/555 |
| 5,903,341 A | * | 5/1999 | Perry et al. ............... | 356/237.1 |
| 5,954,206 A | | 9/1999 | Mallon et al. ............... | 209/580 |
| 6,005,346 A | | 12/1999 | Shaffner ...................... | 313/637 |
| 6,013,887 A | | 1/2000 | Satake et al. ................ | 209/581 |
| 6,078,018 A | * | 6/2000 | Davis et al. ................. | 209/580 |
| 6,410,872 B2 | * | 6/2002 | Campbell et al. ........... | 209/577 |

* cited by examiner

*Primary Examiner*—Donald P. Walsh
*Assistant Examiner*—Daniel K Schlak
(74) *Attorney, Agent, or Firm*—Wells St. John P.S.

(57) ABSTRACT

An article sorting apparatus and method is disclosed and which conveys a mixture of articles on a conveyor belt and through an inspection zone, and which includes at least one illumination source emitting red, green, and infrared radiation for illuminating the articles in the inspection zone; a detector system for sensing the red, green, and infrared radiation reflected from the articles in the inspection zone, and which generates red data, green data, and infrared data; a processor receiving the red data, green data, and infrared data and which generates article sorting data; and a sorter responsive to the sorting data for separating the articles into acceptable articles and unacceptable articles.

4 Claims, 10 Drawing Sheets

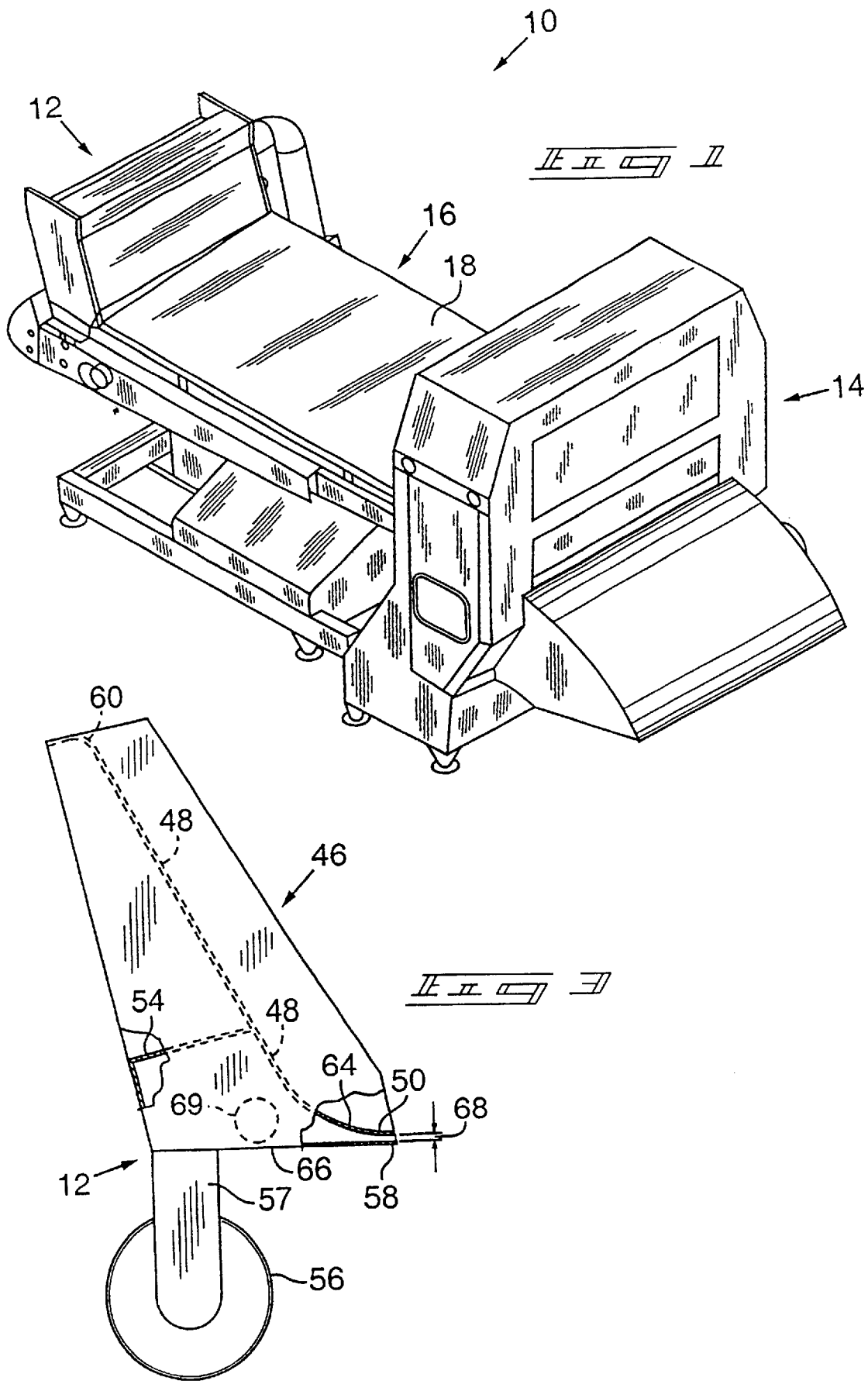

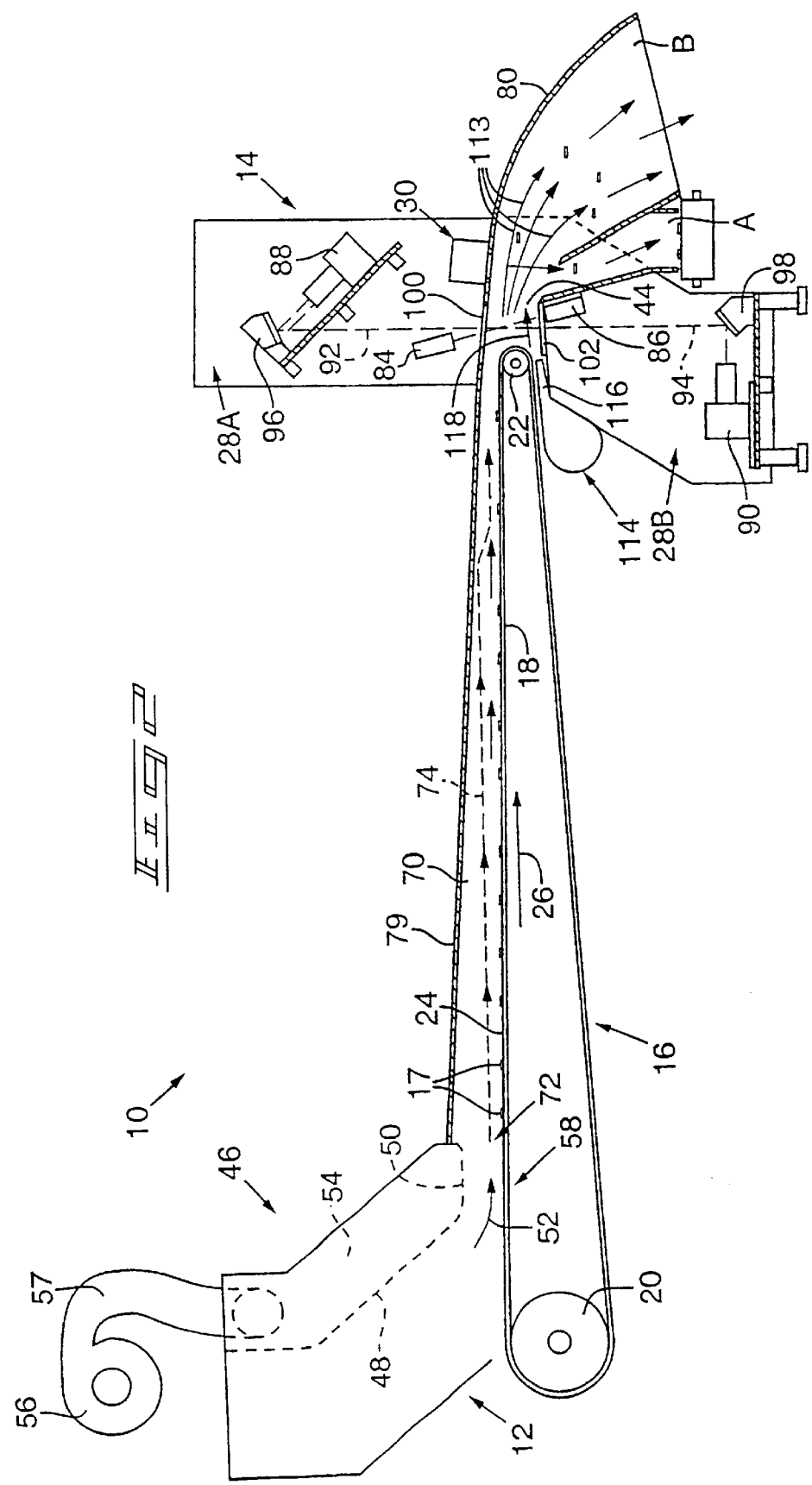

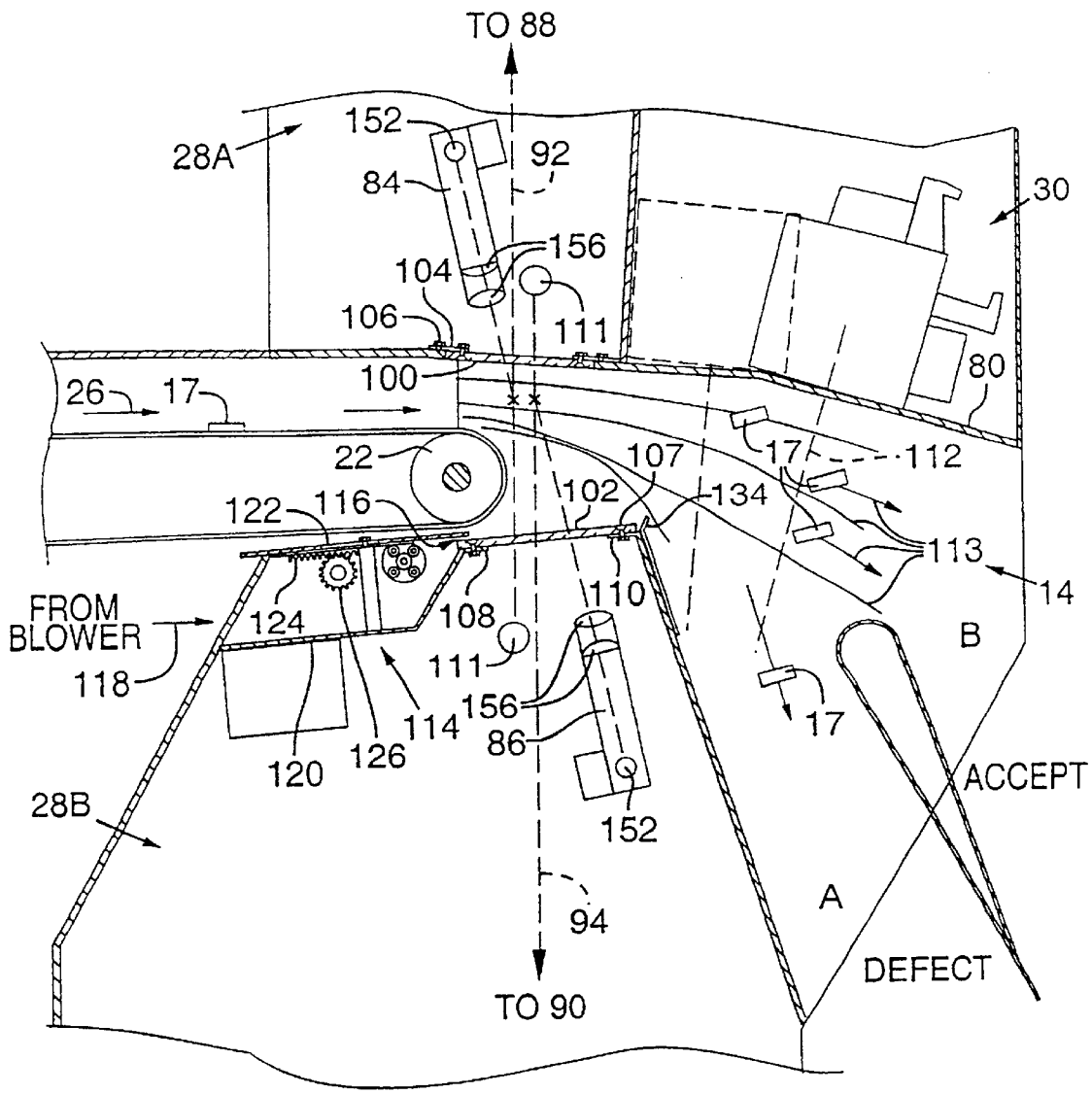

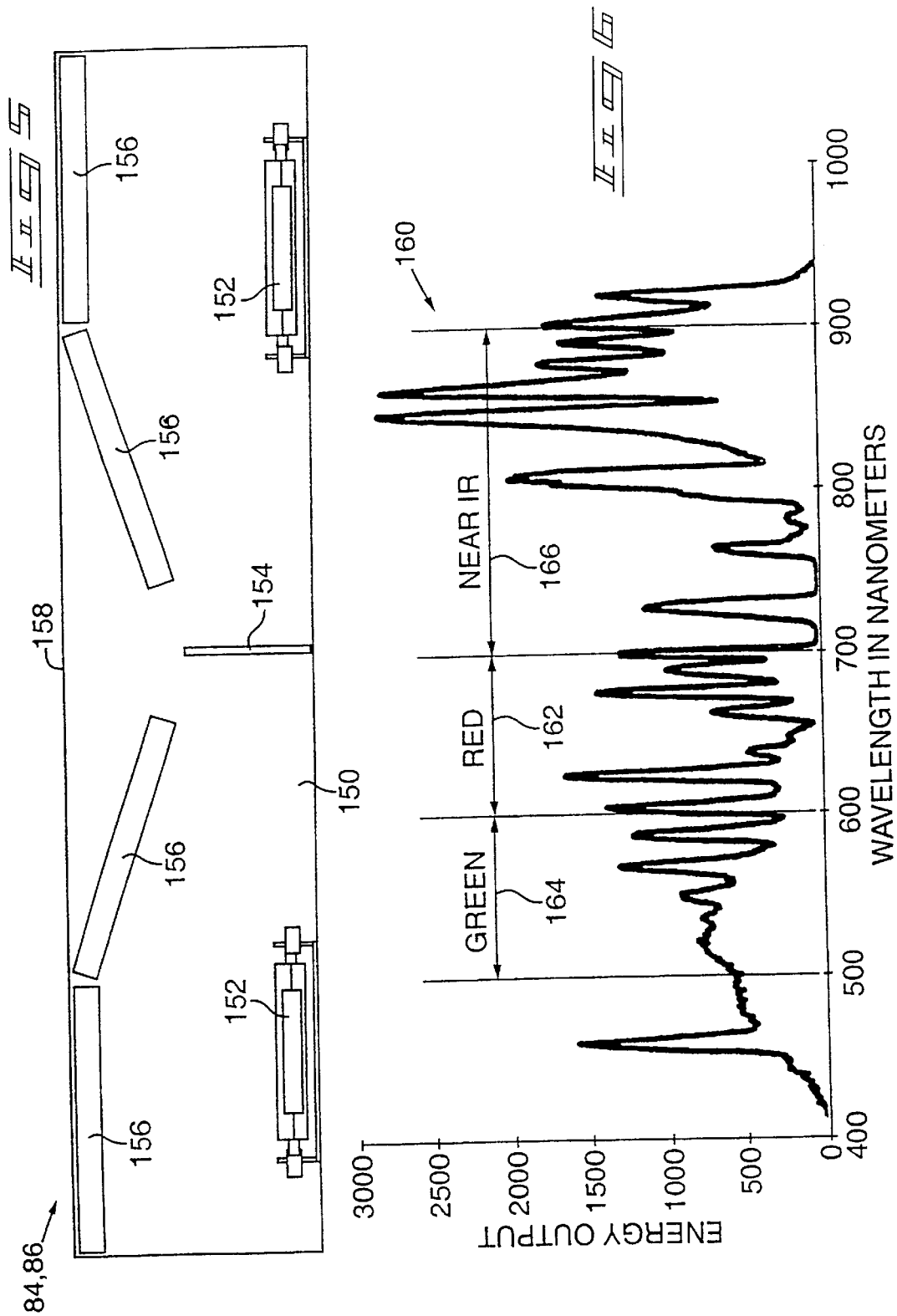

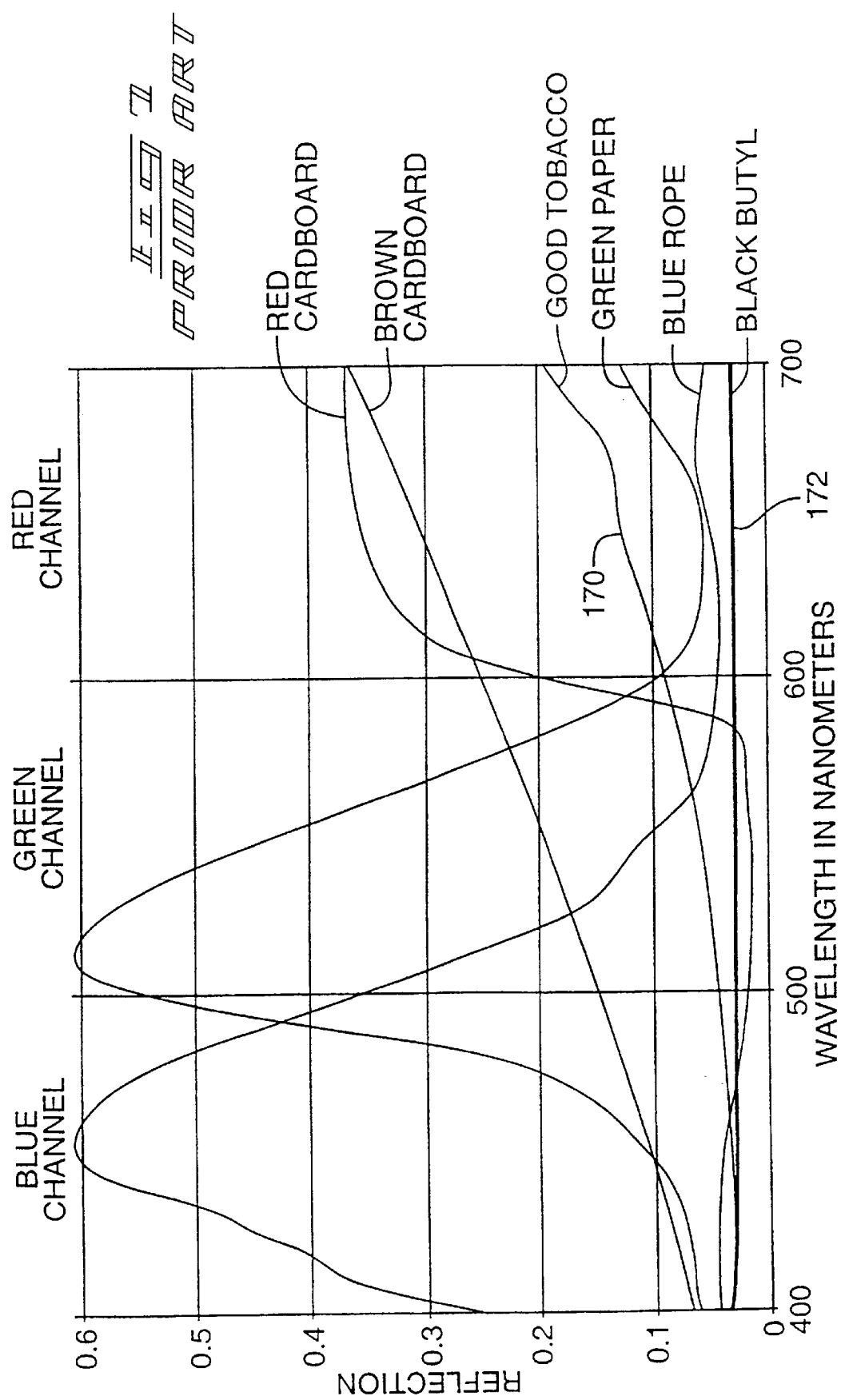

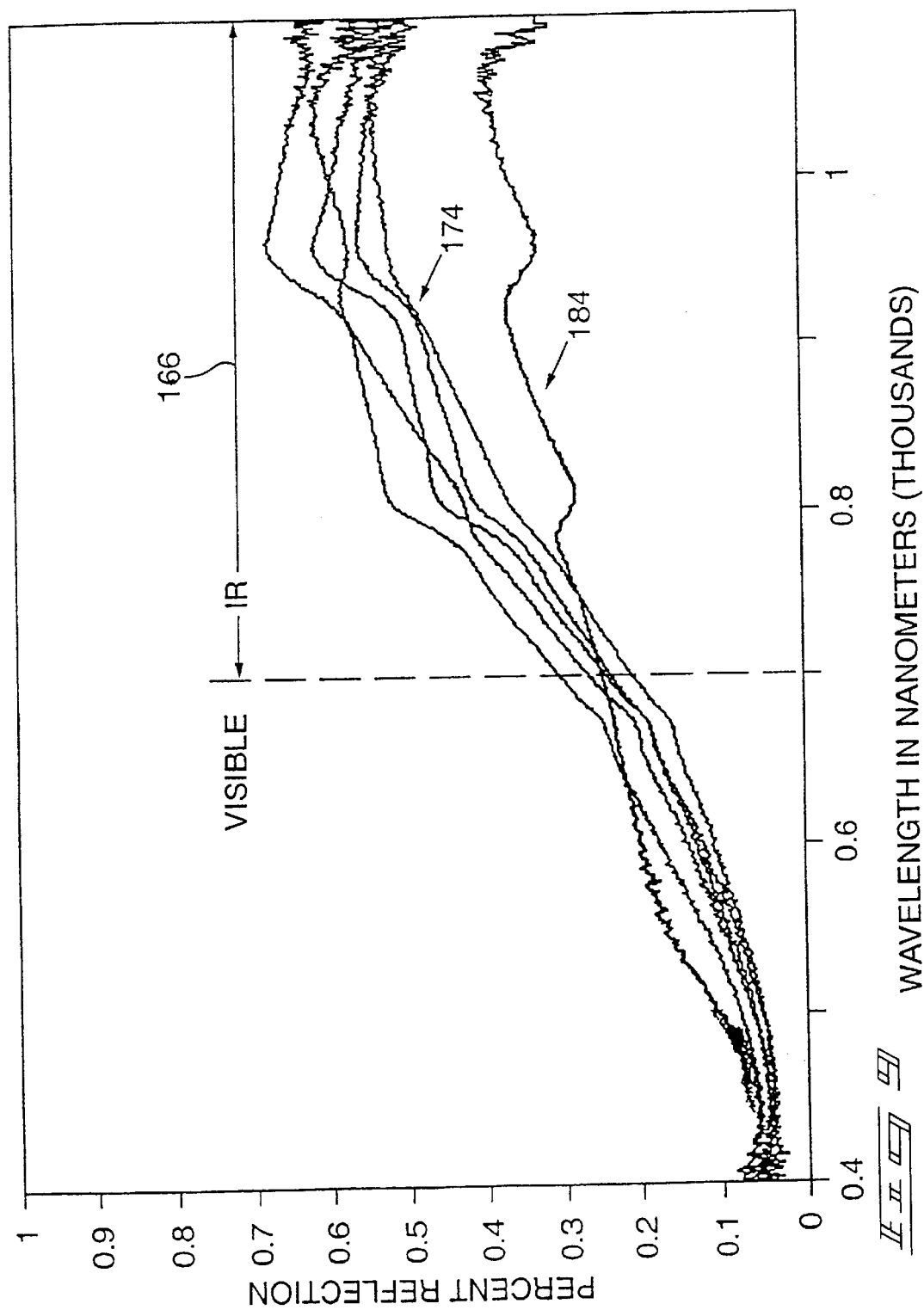

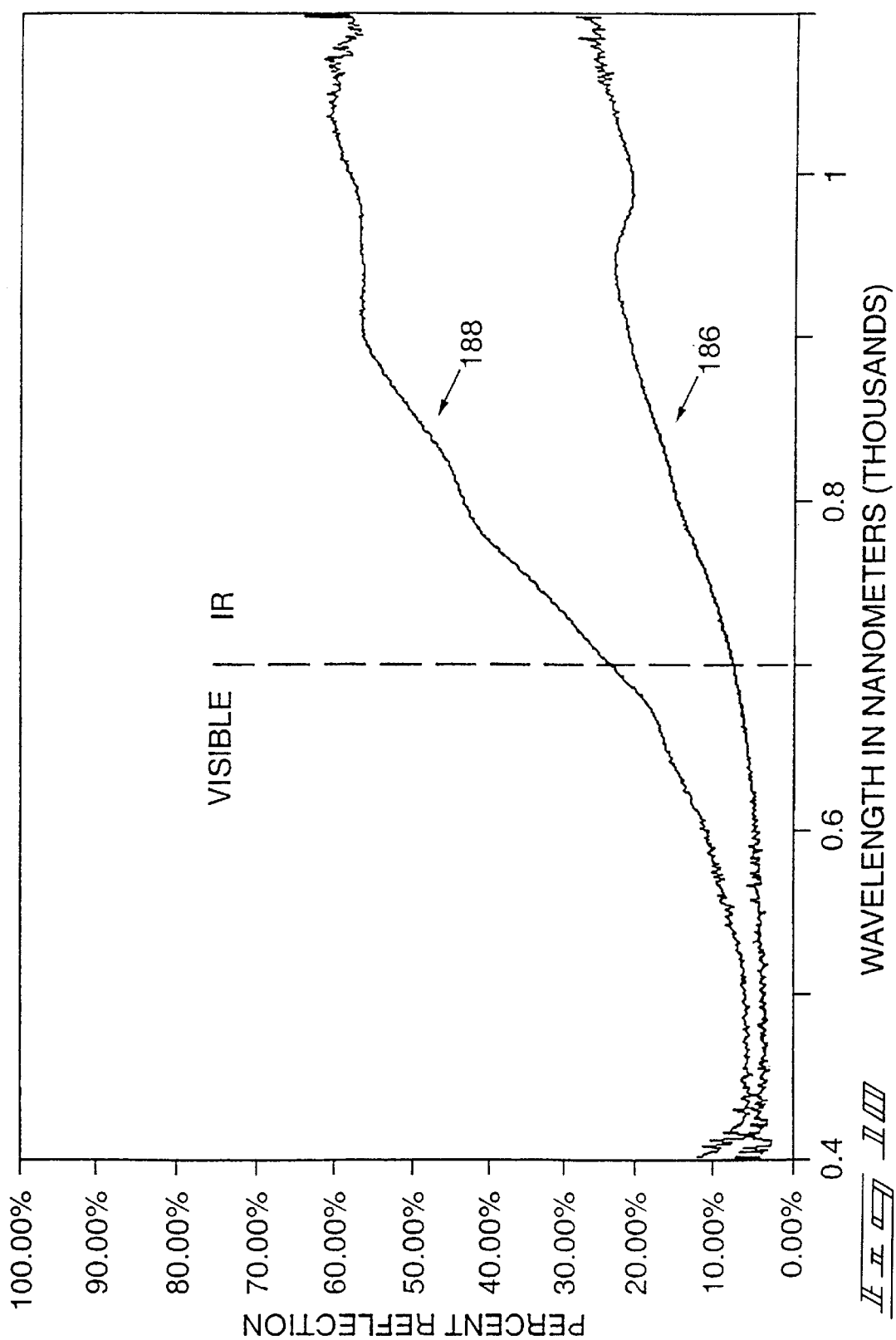

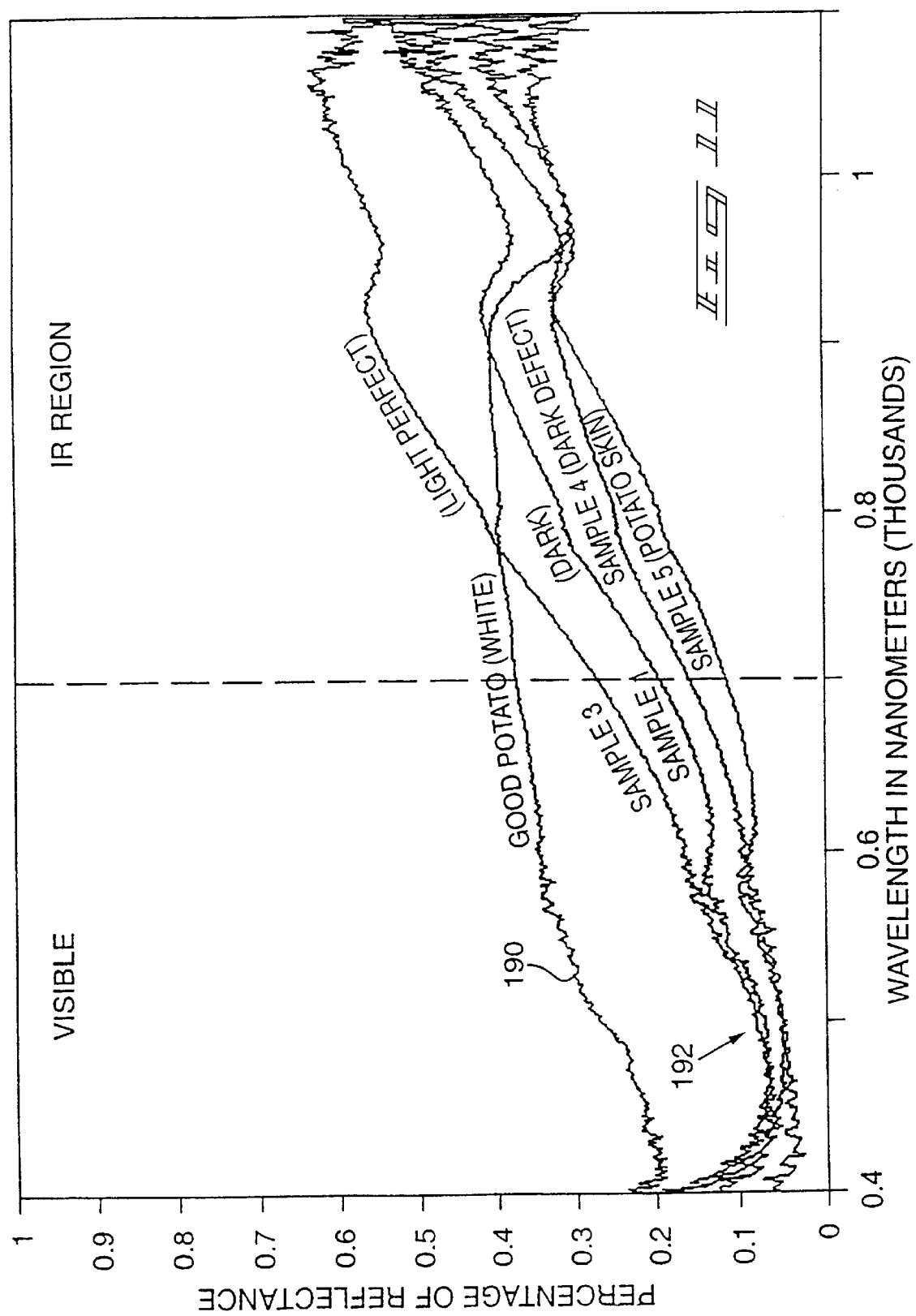

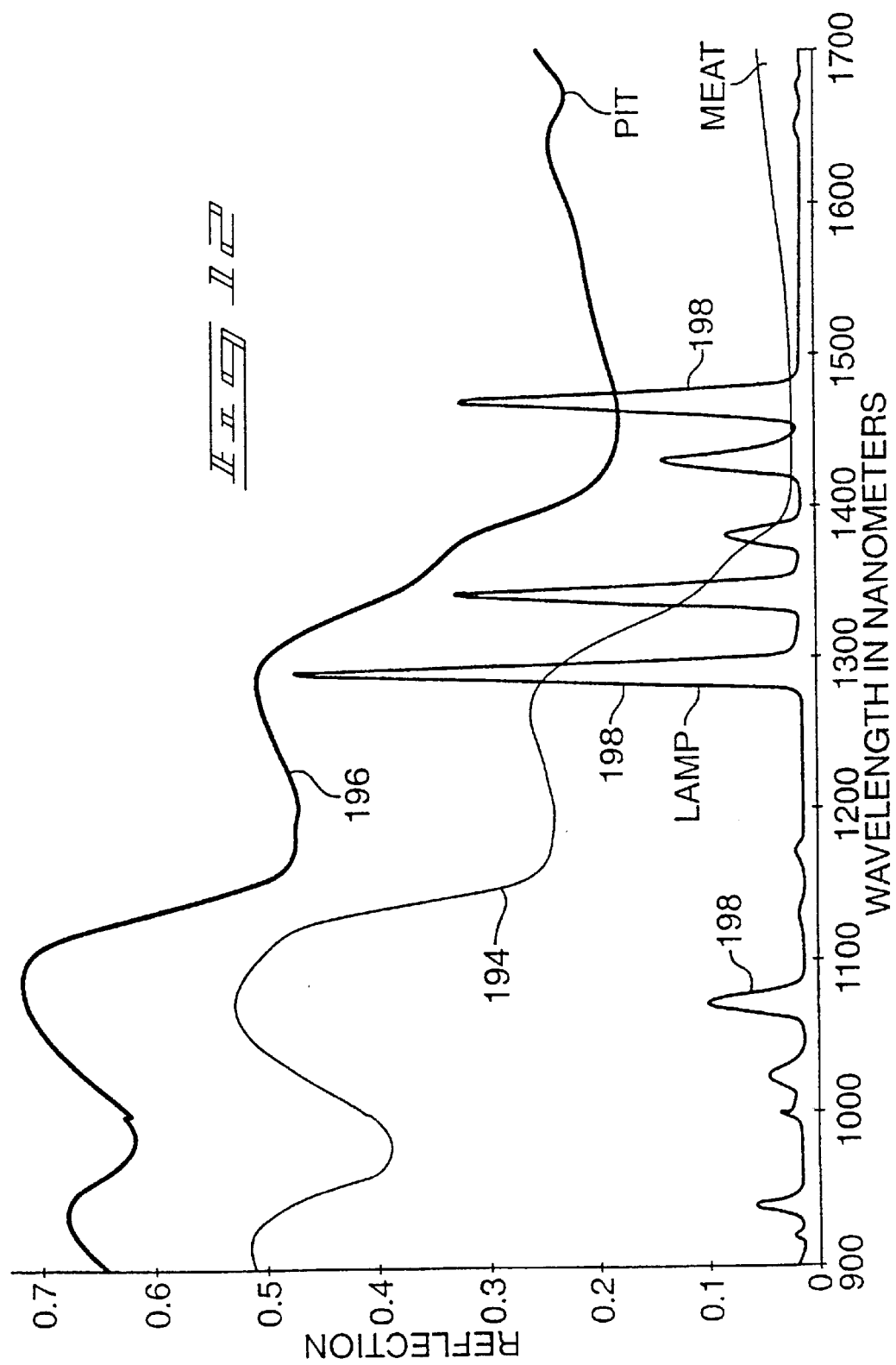

MULTI-BAND SPECTRAL SORTING SYSTEM FOR LIGHT-WEIGHT ARTICLES

CROSS REFERENCE TO RELATED APPLICATION

A This patent application claims priority from PCT number PCT/US00/08384, entitled "Multi-Band Spectral Sorting System for Light-Weight Articles" which was filed Mar. 29, 2000 (29.03.00), and was published in English which claims priority from the Provisional Application No. 60/126,772 entitled "Multi-Band Spectral Sorting System for Light-Weight Articles" which was filed Mar. 29, 1999 (29.03.99) and was published in English.

TECHNICAL FIELD

This invention relates to automated bulk inspection and processing systems and, in particular, to multi-band optical inspection and sorting of light-weight articles, such as stripped-leaf tobacco or laminae, tobacco stems, and reclaimed tobacco.

BACKGROUND OF THE INVENTION

Automated bulk optical processing equipment can perform a variety of tasks such as, for example, inspecting or sorting bulk articles including raw or processed fruit, vegetables, wood chips, recycled plastics, and other similar products. The articles may be classified according to size, color, shape, or other qualities. Modern bulk optical processing equipment can rapidly classify and separate very large quantities of such articles into numerous categories.

Such equipment typically includes a conveyor system for moving the articles past an inspection station where cameras or other detection devices examine the articles as they pass through an inspection zone. The inspection station sends signals to a sorting or treatment station where the articles are sorted or otherwise treated by category. For example, defective or foreign articles may be removed from the flow of articles carried by the conveyor system.

Rapid inspection or sorting of large quantities of articles typically requires high-speed conveyor systems such as, for example, conveyor belts with widths of two to six feet (0.6 to 1.8 meters) that convey the articles at speeds of over 17 feet per second (5 meters per second). A problem conveying articles at such speeds is that light-weight articles are relatively unstable and tend to roll, tumble, bounce, and collide with one another. Unstable articles carried by a high-speed conveyor system are difficult to inspect, sort or otherwise process for at least two reasons.

First, automated bulk optical processing equipment includes cameras or other optical detectors that optically determine selected characteristics of the articles (e.g., size, color, and shape). The rolling, tumbling or bouncing of an article typically diminishes the clarity with which an image of the article is generated, thereby decreasing the accuracy and reliability of the optical information about the article. As extreme examples, rolling could cause a cubic article to appear round, or an article with differently colored regions could appear to have a single mixed color.

Second, unstable articles can move laterally and/or longitudinally relative to direction of conveyor belt travel. Lateral article movement is undesirable because it misaligns the articles as they pass from the inspection station to the processing station, thereby resulting in incorrect processing. Similarly, longitudinal article movement along the direction of belt travel causes effective speed differences that place the articles in temporal misalignment for subsequent processing operations.

Some articles have increased susceptibility to unstable motion on a conveyor, such as light-weight articles and articles of low and non-uniform density. Particular examples of such articles include stripped-leaf tobacco or laminae, tobacco stems, and reclaimed tobacco. Other examples include undesirable debris such as, for example, feathers, paper, cardboard, plastic, string, rope, dirt, twigs, stones, insects, animal parts, and rubber that may incidentally be included within the acceptable articles. As a consequence, these types of articles are difficult to inspect and sort accurately at high speeds.

One attempt to solve such instability problems can be seen in U.S. Pat. No. 5,297,667 for A SYSTEM FOR STABILIZING ARTICLES ON CONVEYORS, which assigned to the assignee of this patent application. This device uses a hood located just above the belt to create a flow of gas (e.g., air) projected along the conveyor belt in a direction generally parallel to that in which the articles are carried by the belt. The air flow has a velocity substantially the same as that above the belt to reduce aerodynamic resistance that would otherwise bear against the articles causing them to become unstable. Since this resistance is reduced, the articles carried by the belt are relatively stable. The articles are accelerated by and propelled from the belt in-air along a known and predictable trajectory to a sorting or processing station. The successful operation of the sorter or processor depends on the products being propelled along the known trajectory. Thus, the processor notes the exact position of the articles as they pass by and can separate defective or undesirable articles from the volume of acceptable articles. This type of system has been successful for articles having a relatively high mass. Articles with high mass are able to maintain their velocity in-air as they are projected from the belt and continue along their predicted trajectory.

Another attempt to stabilize articles as they are moved along a conveyor belt is the use of a second counter-rotating conveyor belt located above and close to the conveyor belt on which the articles are positioned. Instead of blowing air through a hood that encloses the conveyor belt, the second counter-rotating conveyor belt creates a flow of air in a direction generally parallel to the direction of travel of the articles. The flow of air generated by the second counter-rotating conveyor belt has a velocity about the same as the article-conveying belt to reduce any aerodynamic resistance that would otherwise bear against the articles. One example of such a system is the Tobacco Scan 6000 manufactured by Elbicon located near Brussels, Belgium.

However, these systems are inadequate for very light articles such as the above-described tobacco products and light-weight debris or articles weighing about 1.5 to five pounds per cubic foot. Light-weight articles become unstable after they leave the belt and travel along an unknown trajectory. This happens because air flow becomes unstable after it leaves the belt. The air profile separates into a random flow pattern. A portion of the air flows downward while another portion flows straight. Yet other parts of the air may flow upward or in a direction transverse to the direction of travel of the belt. The light-weight articles do not have enough mass to continue along a predicted trajectory. They lose velocity and are drawn into a random air flow pattern. The positions of the articles cannot be predicted at a specific time. This makes accurate processing of the articles difficult and impractical.

Another problem with existing systems is inadequate illumination, detection, and sorting of the articles and, in particular, tobacco products that may include black butyl rubber particles, tobacco-stained latex rubber glove debris, brown cardboard, red cardboard, green paper, and blue plastic rope. The black butyl rubber particles may be contaminants from the rubber-wrapped piping systems that transport cooling water in tobacco processing facilities, or they may be intentionally added to the particle flow to test the inspection and sorting capabilities of the system. The tobacco-stained latex rubber glove debris contaminates the tobacco products as a result of handling by latex-gloved human laborers. Unfortunately, because these particular rubber particles are so visibly similar to tobacco products, that are difficult to detect with present inspection systems. The other contaminants are bits and pieces of containers and packaging employed in transporting and storing the tobacco products. Because of their colors, conventional sorting techniques render some of them difficult to distinguish from the good tobacco products.

What is needed, therefore, is a suitable conveyor for light-weight articles, such as tobacco products, combined with an inspection system that can detect and classify tobacco products containing butyl, latex, and other debris

SUMMARY OF THE INVENTION

An object of this invention is, therefore, to provide an improved conveyor for use with automated bulk processing equipment.

Another object of this invention is to increase stability of light-weight articles as they are carried on and projected in-air from such conveyors.

A further object of this invention is to provide such a conveyor that is capable of allowing increased accuracy in optical processing of light-weight articles and articles of low and non-uniform density.

Still another object of the invention is to provide a system with multi-spectral illumination and sorting of the articles and, in particular tobacco products.

An off-belt stabilizing system of this invention stabilizes light-weight articles as they are projected in-air from a conveyor belt for automated bulk processing equipment. In a preferred embodiment, the light-weight articles are stabilized along a conveyor belt from a first infeed end to a second discharge end. The off-belt stabilizing system provides a totally enclosed system that stabilizes the light-weight articles as they are projected in-air from the second discharge end of the conveyor belt. The air flow at and past the end of the belt is controlled by a hood structure so that light-weight articles that are projected within the air flow travel along a known and predictable trajectory.

This invention also includes improved multi-spectral illumination and sensing of the articles, which is achieved by incorporating a pair of oppositely facing optical illuminating stations and a sorting station into the off-belt stabilizing system. Windows are provided in upper and lower surfaces of the hood structure through which the illumination stations provide red ("R"), green ("G"), and infrared ("IR") illumination (or other wavelength combinations) of both major surfaces of the articles as they pass by an associated pair of line-scanning "color" cameras. Dichroic prisms render the cameras sensitive to the R, G, and IR wavelengths of the illumination stations. The windows extend between the illumination stations and the articles as they travel in-air through the stabilizing system and along their trajectory.

R, G, and IR illumination provides sufficiently differing ratios of reflected R, G, and IR radiation that are usable for making reliable article classification sorting decisions for the above-described tobacco and other products.

Additional objects and advantages of this invention will be apparent from the following detailed description of a preferred embodiment thereof that proceeds with reference to the accompanying drawings.

BRIEF DESCRIPTION OF THE DRAWINGS

FIG. 1 is an isometric view of an automated bulk processing system with an off-belt stabilizing system and R, G, and IR illumination and detection system of this invention.

FIG. 2 is a schematic side view of the automated bulk processing system of FIG. 1.

FIG. 3 is an enlarged sectional side view of an alternative infeed chute and associated components of an on-belt second stabilizing system shown in FIG. 1.

FIG. 4 is an enlarged schematic side view of the off-belt stabilizing system and R, G, and IR illumination and detection system of this invention.

FIG. 5 is a pictorial plan view of an R, G, and IR article illumination unit of this invention.

FIG. 6 is a graphical representation of energy output spectrum produced by the article illumination unit of FIG. 5.

FIG. 7 is a graphical representation of prior art R, G, and blue ("B") energy wavelengths reflected from good tobacco products and various defects.

FIGS. 9, 10, 11, and 12 are graphical representations of visible and IR wavelength reflectance curves for, respectively, tobacco products and stained latex, raisins and stems, good potato flesh and defects, and peach meat and peach pits.

DETAILED DESCRIPTION OF A PREFERRED EMBODIMENT

Figure 8:
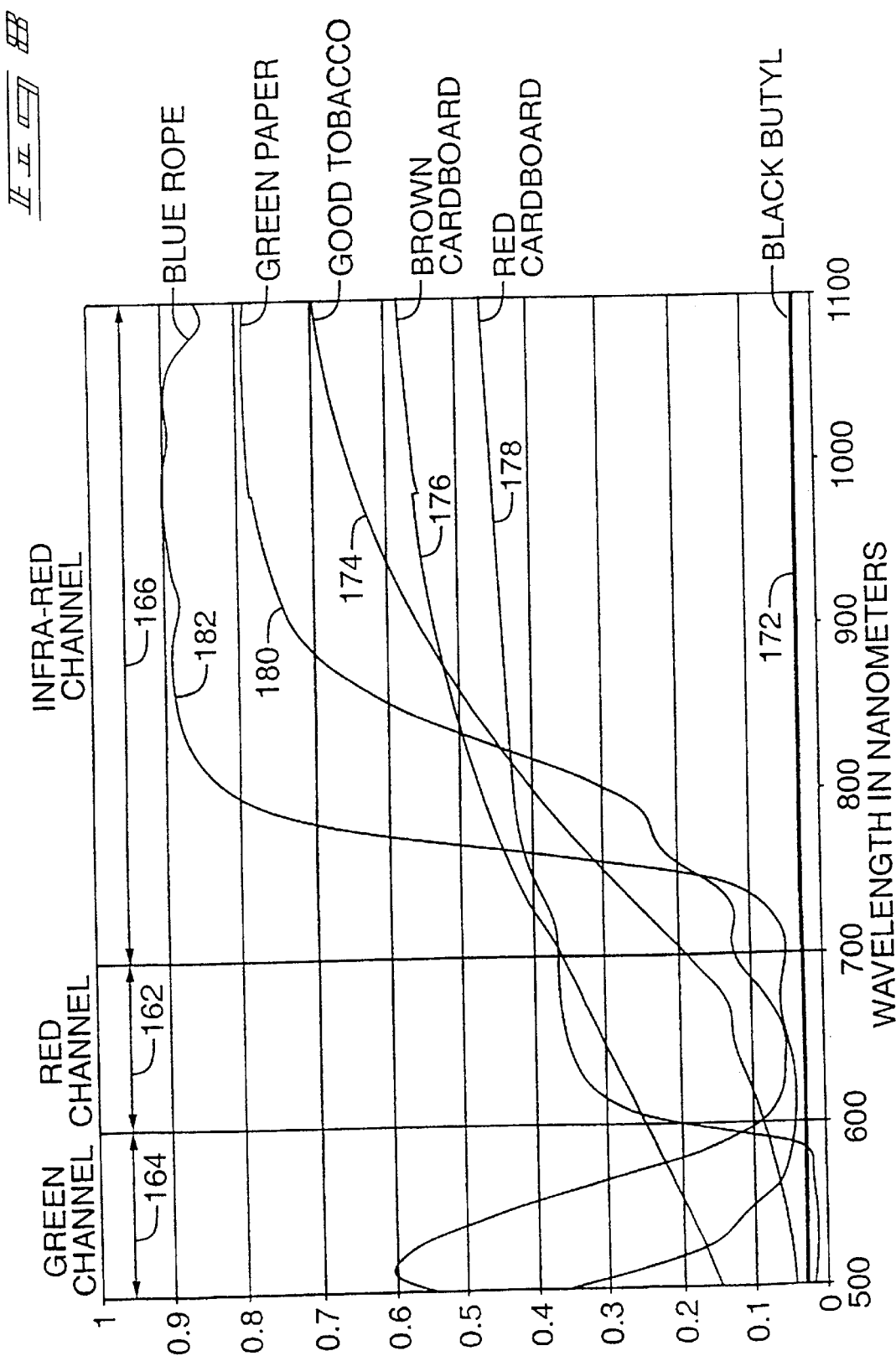
FIG. 8 is a graphical representation of R, G, and IR energy wavelengths reflected from good tobacco products and various defects in accordance with illumination and detection techniques of this invention.

FIGS. 1 and 2 show an automated bulk optical processing system 10 of this invention that includes an on-belt stabilizing system 12 and an off-belt stabilizing system 14 for stabilizing articles carried by a conveyor 16. Optical processing system 10 is based on one described in copending U.S. patent application Ser. No. 08/657,357, filed Jun. 3, 1998 for OFF-BELT STABILIZING SYSTEM FOR LIGHT-WEIGHT ARTICLES, which is assigned to the assignee of this application. Processing system 10 preferably performs optical inspection of large quantities of light-weight articles such as, for example, stripped-leaf tobacco or laminae, tobacco stems, re-claimed tobacco, wood chips, or light-weight debris. It will be appreciated, however, that stabilizing systems 12 and 14 could be similarly employed by other types of automated processing equipment such as, for example, packaging systems.

Conveyor 16 carries articles 17 (FIG. 2) on a commercially available anti-static belt 18 known and used by those having ordinary skill in the art. This type of belt reduces any static charge that may develop during operation. Static charge in belt 18 may cause articles 17 to adhere thereto and reduce the effectiveness of the system. Belt 18 forms a closed loop around a drive roller 20 and a spaced-apart, free-running end roller 22. A motor (not shown) coupled to drive roller 20 drives belt 18 such that an upper surface 24 moves at a velocity in a direction 26 toward off-belt stabilizing system 14 that includes upper and lower optical inspection stations 28A and 28B and a sorting station 30.

Articles 17 are delivered to belt 18 by an infeed system 46 that has an angled chute 48 down which articles 17 slide and are accelerated to about half the velocity of upper surface 24 of belt 18. Articles 17 slide off a lower end 50 of chute 48 and drop onto belt 18. Infeed system 46 could alternatively employ an infeed conveyor belt, and inactive chute, or a vibrating chute.

On-belt stabilizing system 12 helps to accelerate articles 17 dropping from chute 48 to the speed of belt 18 by generating a flow 52 of fluid, preferably a readily available gas such as air, that passes between belt 18 and lower end 50 of chute 48. Air flow 52 engages articles 17 as they drop from chute 48 onto belt 18 and functions to accelerate the articles to the velocity of belt 18. Air flow 52 has a velocity that may, but need not, equal the velocity of belt 18. After articles 17 are accelerated to at or about the velocity of belt 18, air flow 52 functions to stabilize the articles on belt 18.

More specifically, without stabilization, articles 17 dropped onto belt 18 from chute 48 would typically bounce, tumble, and roll, thereby requiring a significant length of belt 18 before articles 17 would settle into moderately stable positions. However, stabilizing system 12 settles articles 17 onto belt 18 much more quickly, thereby allowing belt 18 to be shortened and processing system 10 to be more compact or allowing conveyor 10 to increase product flow with the same stability and greater process throughput.

Referring to FIG. 3, on-belt stabilizing system 12 may alternatively employ a chamber or plenum 54 that receives pressurized air from a blower 56 via a conduit 57. A nozzle 58 in plenum 54 is positioned below and extends across chute 48 and belt 18 to provide a generally smooth flow 52 of air for stabilizing articles 17. Belt 18 carries the articles to off-belt stabilizing system 14 for processing.

Infeed system 46 receives articles 17 at a receiving end 60 of chute 48 from an infeed shaker, conveyor belt, pin feeder, or the like (none shown). Articles 17 are accelerated by gravity as they slide along chute 48 through a bend 64 toward lower end 50. Chamber or plenum 54 is positioned below chute 48 and receives pressurized air from blower 56. Bend 64 in chute 48 cooperates with a slanted bottom surface 66 of plenum 54 to form nozzle 58 that extends across the width of belt 18. In a preferred embodiment, nozzle 58 forms an opening with a height 68 of about 0.25 in (0.64 cm).

To further reduce static charges, ionized air is preferably used to create the flow 52. The air is ionized by passing the air in plenum 54 across an ion bar 69 mounted in any desired fashion within the plenum 54. Ion bar 69 extends across the width of the belt 18 and is of the type known and used by those skilled in the art.

Although a specific infeed system 46 is shown and described, skilled workers will understand that this invention is not limited to the configuration shown and described and that other infeed systems could be used to introduce the lightweight articles onto a conveyor so that they have a velocity substantially the same as the velocity of belt 18.

On-belt stabilizing system 12 further includes a tunnel 70 that extends from an entrance 72 and along the length of and generally enclosing upper surface 24 of belt 18. Tunnel 70 allows stabilizing system 12 to form and propagate a flow 74 of fluid, preferably a readily available gas such as air, that passes over and past the length of belt 18. Tunnel 70 is formed by a hood 79 positioned over and extending along belt 18.

Skilled workers will understand that any on-belt stabilizing system may be used to stabilize the light-weight articles on conveyor belt 18. For example, a dual conveyor belt system such one used in the Tobacco Scan 6000 manufactured by Elbicon located near Brussels, Belgium, may be used that employs a counter-rotating conveyor belt located above the lower article-bearing conveyor belt. The counter-rotating conveyor belt creates a flow of air between the lower conveyor belt and the counter-rotating conveyor belt to stabilize the articles on the lower conveyor belt.

In a conventional conveyor system not employing an air assisted stabilizing system, only a thin boundary layer of air travels at or near the speed of the conveyor belt. For a smooth conveyor belt, the boundary layer typically extends only a few millimeters above the belt. Articles with thicknesses greater than a few millimeters extend through the boundary layer to slower or generally stagnant air. As a consequence, articles 17, or certain ones of them, may be retarded by the slower-moving air, thereby destabilizing at least some of articles 17 on belt 18, causing them to roll, tumble, bounce or collide with one another.

Air flow 74 induces an air draft along tunnel entrance 72 so that articles 17 carried on belt 18 are gradually stabilized by air flows of increasing velocity. On-belt stabilizing system 12 stabilizes articles 17 carried on belt 18 so that they are substantially stable and travel at substantially the belt velocity toward off-belt stabilizing system 14.

Referring to FIG. 4, off-belt stabilizing system 14 includes an end hood portion 80 that extends through inspection stations 28A and 28B and supports sorting station 30 to provide a closed environment for articles 17 as they are propelled off the end of belt 18.

Inspection station 28A and 28B include respective upper and lower article illumination units 84 and 86 and upper and lower camera modules 88 and 90 to identify selected optical characteristics of articles 17 as they are propelled from belt 18. Upper and lower camera modules 88 and 90 include dichroic prisms that separate the wavelengths of light detected into R (600 to 700 nm), G (500 to 600 nm), and IR (700 to at least 900 nm) wavelength spectrum portions. Suitable prisms are available under specification drawing No. SSB-BA005-01 from Canon U.S.A., Inc., located in Irvine, California. Article illumination units 84 and 86 are rich in R, G, and IR spectral radiation and are described in more detail with reference to FIGS. 4 and 5. Camera modules 88 and 90 view the articles along respective lines of sight 92 and 94 through adjustable mirrors 96 and 98. Inspection stations 28A and 28B identify preselected ratios of R, G, and IR radiation reflected from articles 17 in accordance with methods and processing systems described in U.S. Pat. No. 5,085,325 of Jones et al. for COLOR SORTING SYSTEM AND METHOD, which is assigned to the assignee of this application and incorporated herein by reference.

As best seen in FIG. 4, to illuminate articles 17 as they pass through off-belt system 14 and so that cameras 88 and 90 can properly view articles 17, upper and lower transparent windows 100 and 102 are mounted within end hood portion 80. Windows 100 and 102 may be constructed of any durable transparent material, such as, for example, glass or plastic. Upper window 100 may be mounted by, for example, brackets 104 and fasteners 106. Lower window 102 may be secured by, for example, fasteners 107 to flanges 108 and 110 of end hood portion 80. These windows protect article illumination units 84 and 86 from articles 17 and from any other debris that may be included within the flow of articles. Article illumination units 84 and 86 are located substantially close to the lines of sight 92 and 94 of articles 17 without interfering with the field of view of cameras 88 and 90. Lines of sight 92 and 94 are offset from one another and may terminate at background lamps 111, which provide either a contrasting or noncontrasting background color for cameras 88 and 90 to view while inspecting radiation from upper and lower article illumination units 84 and 86 reflected off articles 17. Background lamps 111 are preferably fluorescent tubes providing a noncontrasting background color similar to the color of tobacco products.

Cameras 88 and 90 view articles 17 along scan lines (shown end-on as X's) that extend transverse to direction 26 of travel of the belt 18. The scan lines have a length substantially the same as the width of belt 18 so that articles 17 anywhere along the width of belt 18 are viewed by cameras 88 and 90. Upper and lower article illumination units 84 and 86 are elongated and mounted to extend transverse to direction 26 of travel of belt 18 and are, therefore, parallel to scan lines X. Upper and lower article illumination units 84 and 86 cannot be exactly collinear with scan lines X because they would block the view of the cameras 88 and 90 and would cause specular reflections off windows 100 and 102 into the cameras. However, Upper and lower article illumination units 84 and 86 are substantially more collinear with the scan line than has been possible in prior systems. Thus, improved illumination of the articles 17 is provided. This placement of lamps relative to scan lines X causes focused radiation to illuminate articles 17 for the respective camera without interfering with the illumination for the other camera. Because light-weight articles, such as tobacco products, may be somewhat transparent, radiation transmitted through the articles can create false color indications. The preferred geometry and illumination source of this-invention combine to solve the problem. Upper and lower article illumination units 84 and 86 are described in more detail with reference to FIG. 5.

After articles 17 pass through inspection stations 28A and 28B, sorting station 30 employs multiple "puff jets" 112 positioned downstream of but substantially across the width of belt 18 to produce pressurized air blasts directed through an access opening (not shown) in end hood portion 80 to divert selected (typically defective) ones of articles 17, which would otherwise be propelled along normal trajectories 113 from belt 18. Defective articles 17 may be diverted by sorting station 30 into a defect chute A, thereby allowing acceptable articles to be propelled into an acceptance chute B.

An air curtain unit 114 having an adjustable nozzle 116 is positioned below end roller 22 and directs an air flow 118 toward normal trajectories 113. Air flow 118 functions to support relatively small or light-weight articles within normal trajectories 113 and prevents the light-weight articles from being drawn around and under roller 22 by turbulent air flow.

Air curtain 114 has a housing 120, a top 122 of which is horizontally adjustable by a rack 124 and pinion 126 that may be rotated either manually or by a motor (not shown) to adjust the nozzle opening 116 through which the air is directed and allows control of air flow 118. Air flow 118 further acts to clean lower window 102 of any debris or dust. To prevent static charge from building up on the lower window 102, an ion bar 128, similar to ion bar 69 employed within plenum 54, is located within air curtain unit 114.

In a preferred embodiment, processing system 10 conveys, inpects, and sorts tobacco leaf products, wood chips, or debris with belt 18 having a width of 2–6 ft (0.6–1.8 m) and driven at a velocity of up to about 1,500 ft/min (7.6 m/sec). Stabilizing system 12, with nozzle 50 having a height of 0.25 in. (0.006 m) through which air flow 52 is driven at 10,000 ft/min (50.8 m/sec), displaces about 850 ft$^3$/min (24.1 m$^3$/min) (standard). Air curtain unit 114, with nozzle 116 having an opening height of 0.125 in (0.32 cm) through which air flow 118 moves up to 6000 ft/min (30 m/sec), displaces 276 ft$^3$/min (7.82 m$^3$/min) (standard).

As articles 17 leave belt 18, they are completely enclosed within end hood portion 80 as they are projected past optical inspection stations 28A and 28B and sorter station 30. The velocity of articles 17 is uniformly maintained because articles 17 are enclosed within end hood portion 80 and air flow 118 is adjustable. Therefore, articles 17 travel along more predictable trajectories resulting in their more accurate and efficient processing.

FIG. 4 shows in a side, or end-on view of article illumination units 84 and 86, whereas FIG. 5 is a top view revealing internal components thereof. The side and top views together reveal that article illumination units 84 and 86 include an elongated, shallow box-shaped housing 150 that encloses a pair of 1000 watt cesium halide doped high-intensity discharge lamps 152 that are optically separated by a light baffle 154. Four elongated cylindrical lens assemblies 156 are spaced along an open side 158 of housing 150 to project an image of lamps 152 that extends substantially along scan lines X (FIG. 4) to illuminate articles 17 passing therethrough.

FIG. 6 shows a preferred energy output spectrum 160 for lamps 152, which are shown to have significant energy output in a R wavelength region 162 (600 to 700 nm), a G wavelength region 164 (500 to 600 nm), and an IR wavelength region 166 (700 to at least 900 nm). Spectrum 160 provides spectral energy that is suitably matched to the R, G, and IR wavelength sensitivities of camera modules 88 and 90 and which produces a spectral illumination of articles 17 that provides suitable contrast between good tobacco products and foreign materials.

Camera modules 88 and 90 (FIGS. 2 and 4) detect the spectral energy reflected from articles 17 and foreign materials and provide "pixel" signals representative of the reflected energy distributed along scan lines X. Camera modules 88 and 90 convert the reflectance values into voltages (0 to 1 volt) and analog-to-digital converters ("ADCs", not shown) generate binary numbers from the voltages (0 to 256 dec, 00 to FF hex) in direct proportion to reflectance value. For example, the hex values might be 1E, 0C, 99 for the R, G, and IR signals respectively. This is:formed into a binary address where the G 8 bits form the most significant portion of a 24-bit word and the IR 8 bits form the least significant portion of the 24-bit word. The resulting 24-bit word is applied as an address into a lookup table. Stored at the 24-bit address would be the a binary value "0" indicating a defect or a binary value "1" indicating an acceptable article. These pixel by pixel lookup table decisions are grouped for size filtering and the appropriate puff jets 112 (FIG. 4) activated to deflect the defective articles down defect chute A (FIG. 4).

EXAMPLES

FIG. 7 shows the spectral reflectance curves of good tobacco products 170 and various typical defects as detected in conventional R, G, and B (blue) inspection and sorting systems. In this conventional spectral region there is insufficient distinction between the reflectances of black butyl defects 172 and good tobacco. Because of the typical 10% reflectance variations over large samples of articles, it is not surprising that black butyl defects 172 are difficult to separate from good tobacco products 170.

FIG. 8 shows the spectral reflectance curves of good tobacco products 174 and various typical defects as detected in the R, G, and IR inspection and sorting system of this invention. These curves show a rapid reflectivity increase for good tobacco products 174 in IR wavelength region 166, whereas the reflectivity of black butyl defects 172 remains consistently low. If black butyl defects 172 were the only defects, then a camera sensing only IR wavelength region 166 would be capable of sorting this defect. Unfortunately, the other defects, such as brown cardboard 176, red cardboard 178, green paper 180, and blue plastic rope 182 also show a reflectivity increase in IR wavelength region 166. To ensure reliable sorting decisions, the ratios of the R, G, and IR reflected energies are considered.

Consider first the reflectivity of blue plastic rope 182. In R wavelength region 162, the average reflectance is about 5%, and in IR wavelengths region 166 from 700 to 900 nm the reflectance is about 60%. Camera modules 88 and 90 convert these reflectances into voltages and the ADCs generate binary numbers proportional to reflectance. For blue plastic rope 182, the hex values might be 1E, 0C, and 99 for the R, G, and IR signals respectively. A processor concatenates these values to form a binary address where the G 8 bits form the most significant portion of a 24-bit word and the IR 8 bits form the least significant portion of the 24-bit word. This 24-bit word is applied as an address into a lookup table. Stored at this address would be the binary value for "0" indicating that blue rope is a defect.

Similarly the 24-bit word for black butyl defects 172 might be 07, 07, 07. At that address and in close proximity thereto, would be found the binary value "0" indicating that black butyl is also a defect.

Good tobacco products 174 might have values of 0F, 21, 66. At that address would be found a binary value "1" indicating that good tobacco products 174 have been detected and should not be removed.

Skilled workers will recognize that portions of this invention may be implemented differently from the implementation described above for a preferred embodiment. For example, R, G, and IR sorting may be employed to detect and sort various other types of articles. For example, FIG. 9 shows spectral reflectance curves suitable for separating good tobacco products 174 from stained latex, FIG. 10 shows spectral reflectance curves suitable for separating raisins 186 from stems 188, FIG. 11 shows spectral reflectance curves suitable for separating good potato flesh 190 from various defects 192, and FIG. 12 shows spectral reflectance curves suitable for separating peach meat 194 from pits 196 or fragments of pit material. FIG. 12 further shows a short-wave IR spectral energy curve 198 generated by an indium iodide-doped lamp suitable for short-wavelength infrared illumination of articles in some applications of this invention.

Cameras modules 88 and 90 need not be used in a dual configuration because a single camera can suitably inspect many articles, although dual cameras are preferred. As an alternative, a cold mirror could be inserted in lines of sight 92 and 94 for dividing at about 700 nm the reflected energy into separate visible and IR paths. Separate visible- and IR-sensitive cameras or sensors could be arranged to detect the energy in each path.

It will be obvious to those having skill in the art that many changes may be made to the details of the above-described embodiments of this invention without departing from the underlying principles thereof. Accordingly, it will be appreciated that this invention is also applicable to article inspection applications other than those found in agricultural applications. The scope of this invention should, therefore, be determined only by the following claims.

We claim:

1. A method for sorting tobacco products, comprising:

providing a conveyor belt having an infeed end, an opposite discharge end, and an upper supporting surface, and wherein the conveyor belt rotates at a selected speed;

enclosing the upper supporting surface of the conveyor belt with a hood, the hood extending from the infeed end of conveyor belt to the opposite discharge end thereof, the hood defining a tunnel having a continuously diminishing cross sectional dimension when measured in a direction extending from the infeed end of the conveyor to the opposite discharge end thereof;

providing a source of tobacco products to be sorted, and wherein the source of tobacco products is mixed with unacceptable items which are selected from a group which comprises cardboard, paper, rope, black butyl, and stained latex;

depositing the source of tobacco which is mixed with unacceptable items on the infeed end of the conveyor belt;

generating an air flow having a direction of movement within the tunnel, the direction of the air flow moving generally parallel relative to the upper supporting surface of the conveyor belt and from the infeed end to the opposite discharge end, and wherein the air flow has a first velocity at the infeed end of the conveyor, and a second velocity at the opposite discharge end of the conveyor, and wherein the diminishing cross sectional dimension of the tunnel increases the velocity of the air flow as the air flow moves from the infeed end of the conveyor to the opposite discharge end, and wherein the increasing air flow velocity stabilizes the source of tobacco mixed with unacceptable items on the upper supporting surface of the conveyor belt;

providing an inspection zone which is disposed downstream of and in spaced relation relative to the discharge end of the conveyor belt;

illuminating the source of tobacco which is mixed with unacceptable items as they move through the inspection zone with at least one illumination source which emits red, green, and infrared radiation;

sensing the red, green, and infrared radiation reflected from the source of tobacco which is mixed with unacceptable items;

generating red green and infrared radiation data from the red green and infrared radiation sensed in the inspection station;

providing a data processor for receiving and processing the red, green, and infrared radiation data and generating sorting data based upon the red, green, and infrared radiation; and providing a sorter down stream of and in spaced relation relative to the discharge end of the conveyor, and wherein the sorter receives the sorting data from the data processor and separates the tobacco products from the unacceptable items.

2. A method as claimed in claim 1, and further comprising:

generating an article stabilizing air flow which is directed toward the tobacco products and the unacceptable items as they move through the inspection station to cause the tobacco products and the unacceptable items to have a substantially predictable path of travel.

3. A method as claimed in claim 1, and wherein the first velocity of the air flow is equal to or less than the selected speed of the conveyor belt.

4. A method as claimed in claim 1, and wherein the second velocity of the air flow is greater than the first velocity and wherein the second velocity is equal to or greater than the selected speed of the conveyor belt.

* * * * *